United States Patent

Sabin

Patent Number: 6,099,555
Date of Patent: Aug. 8, 2000

[54] GELLING COLD PACK

[75] Inventor: Martin W. Sabin, Nokomis, Fla.

[73] Assignee: Tempra Technology, Inc., Bradenton, Fla.

[21] Appl. No.: 09/127,102

[22] Filed: Jul. 31, 1998

[51] Int. Cl.[7] .................. A61F 7/00; A61F 7/12
[52] U.S. Cl. .............. 607/96; 607/114; 607/108
[58] Field of Search .............................. 607/108, 114; 126/263.01; 62/4

[56] References Cited

U.S. PATENT DOCUMENTS

| | | | |
|---|---|---|---|
| 3,804,077 | 4/1974 | Williams | 126/263 |
| 3,977,202 | 8/1976 | Forusz et al. | 62/4 |
| 4,049,408 | 9/1977 | Patel | 62/4 |
| 4,081,256 | 3/1978 | Donnelly | 62/4 |
| 4,397,315 | 8/1983 | Patel | 128/403 |
| 4,462,224 | 7/1984 | Dunshee et al. | 62/530 |
| 4,780,117 | 10/1988 | Lahey et al. | 62/4 |
| 4,967,573 | 11/1990 | Wilhelm | 62/530 |
| 5,035,230 | 7/1991 | Steidl et al. | 126/263 |
| 5,391,198 | 2/1995 | Cheney, III et al. | 607/114 |
| 5,423,996 | 6/1995 | Salyer | 252/70 |
| 5,478,988 | 12/1995 | Hughes et al. | 219/730 |
| 5,534,020 | 7/1996 | Cheney, III et al. | 607/108 |
| 5,545,197 | 8/1996 | Bowen | 607/108 |
| 5,552,075 | 9/1996 | Salyer | 252/70 |
| 5,611,329 | 3/1997 | Lamensdorf | 126/263.07 |
| 5,650,090 | 7/1997 | Salyer | 252/70 |
| 5,871,527 | 2/1999 | Gubernick | 607/114 |

OTHER PUBLICATIONS

Livage, J., et al., Sol–Gel Chemistry of Transition Metal Oxides, Prog. Solid St. Chem., 18:259 (1988).
U.S. application No. 09/021,927, Sabin et al., filed Feb. 11, 1998.

*Primary Examiner*—Linda C. M. Dvorak
*Assistant Examiner*—Jocelyn Debra Ram
*Attorney, Agent, or Firm*—Fish & Richardson P.C.

[57] ABSTRACT

The present invention provides a cold pack which utilizes the negative heat of solution of a material dissolving in a liquid. The cold pack further includes a gelling agent, which is activatable to form a gel. The gel provides a number of benefits, including better distribution of cold, increased cold persistence in the cold pack, and a more complete utilization of the ingredients of the cold pack than possible with prior art devices.

17 Claims, 2 Drawing Sheets

GELLING COLD PACK

BACKGROUND OF THE INVENTION

The invention relates to a cold pack utilizing the negative heat of solution produced upon the dissolution of a material in a liquid.

Compact, self-cooling devices that produce cold through the negative heat of dissolution of a material in a liquid are known to the art. U.S. Pat. No. 3,804,077 to Williams discloses a cold pack which contains a water-soluble material (ammonium nitrate) and a starch material acting as a gelling agent in one zone, and water in another zone. When a user breaks a separator between the zones, the ingredients are mixed. Dissolution of ammonium nitrate is endothermic, absorbing heat from the surroundings and "producing cold." Starch gels are known to provide some rigidity to cold packs, inhibiting uneven distribution of the mixed contents of the pack under the influence of gravity. The effective cold-providing lifetime of such a cold pack is lengthened, because water is inhibited from reaching the ammonium nitrate as rapidly as would occur in the absence of a gel.

The starch tends to accumulate on the bottom of the pack during shipping, since the materials in the pack have very different particle sizes and densities. The ingredients of such packs are often poorly distributed. Some regions of the pack are overly well gelled, but they are not cold because the gel hinders diffusion of water and ammonium nitrate toward each other. Other regions of the pack may be inadequately gelled, and they are overly cold with a shortened cold-producing lifetime. Before use, the packs should be agitated to attempt to distribute the starch evenly. Uniform distribution is not always possible. This leads to inconsistent pack-to-pack gelling performance and consequently, temperature drop.

Additionally, powdered starch is used in many prior art devices. Powdered starch is used in order to provide rapid gel forming ability in cold solutions. It is very light weight and tends to produce dust during cold-pack manufacture. Starch dust contaminates the seal areas in plastic bag packages, so that imperfect or weak seals are formed. A significant portion of the powder is lost in dust control systems, leading to increased cost for the individual cold packs. Additionally, powdered starch is an extreme explosion hazard, creating unsafe working conditions in factories manufacturing cold packs.

SUMMARY OF THE INVENTION

In one aspect, the invention provides a gelling cold pack including a gelling agent which is adhered as a permeable, preferably liquid permeable, non-continuous coating to a composite particulate "cold-generating" material. This latter material can interact with a liquid second material to produce cold. Cold is produced by the negative heat of dissolution of the composite particulate material into the liquid second material, which is preferably an aqueous solution. The "cold-generating" material can be, for example, one of a number of ammonium salts, tin, cobalt or nickel salts, alkali metal salts or an organic compound such as urea. A preferred "cold-generating" material is ammonium nitrate, especially in the form of a prill, preferredly a low-density ammonium nitrate prill. The gelling material is preferred to be a starch. It can be applied to an ammonium nitrate prill by spraying, dipping, brushing or with the use of an adhesive material. The cold packs can also contain a phase change material, which can provide an extended practical cold-generating lifetime for the device.

These materials are housed in separated liquid-impermeable, heat-conducting zones of a disposable container such that one zone contains the gelling agent-coated particulate "cold generating" material and the other zone contains the liquid material. There can any number of such zones of each type. The disposable container can be made of a polymeric material that conforms to its surroundings.

The gelling cold pack of the invention produces cold by activation of the device, which includes the compromise of a separator between the above-mentioned zones. The separator can be a single-use frangible membrane.

In another aspect, the invention provides a method for cooling objects by contacting an object with the cold pack of the invention, either before or after activation. The activation of the device produces cold, to cool the object, which can be a part of the body of an animal, preferably human, or the object to be cooled can be an item of food or drink.

In another aspect, the invention provides a method of coating ammonium nitrate prills by applying a gelling agent to an ammonium nitrate prill to provide a permeable, non-continuous layer of gelling agent, and drying the prill/gelling agent combination.

The cold packs of the present invention provide a number of advantages. The gelling agent forms a uniformly distributed gel upon operation of the device. The presence of this gel prevents the mixed cold-generating material from settling at the bottom and reducing the efficiency of the device.

The uniform gel also increases the effective lifetime of the device, thereby resulting in a longer time profile of cold generation than previously possible.

The cold packs of the invention have a superior dispersion of gelling agent within the packs. Adhering the gelling agent to the cold-generating material does not allow the gelling agent to "pill", or fail to become substantially wetted as soon as the pack is activated. In cold packs of the invention, the adhered gelling agent does not form a continuous coating over the cold-generating material, and, thus, does not inhibit the onset of the temperature drop associated with activation of the pack.

Manufacture of the cold packs of the invention involves much less dusting of powdered gelling agent, typically starch. Pack sealing is more uniform, and seals are less prone to failure.

The present invention also allows the manufacture of smaller cold packs than was previously possible, also due to the more efficient use of the ingredients. Since all gelling agent is available to be wetted, there is no need to add excess gelling agent to account for an unwetted portion.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF THE PREFERRED EMBODIMENTS

Figure 1:
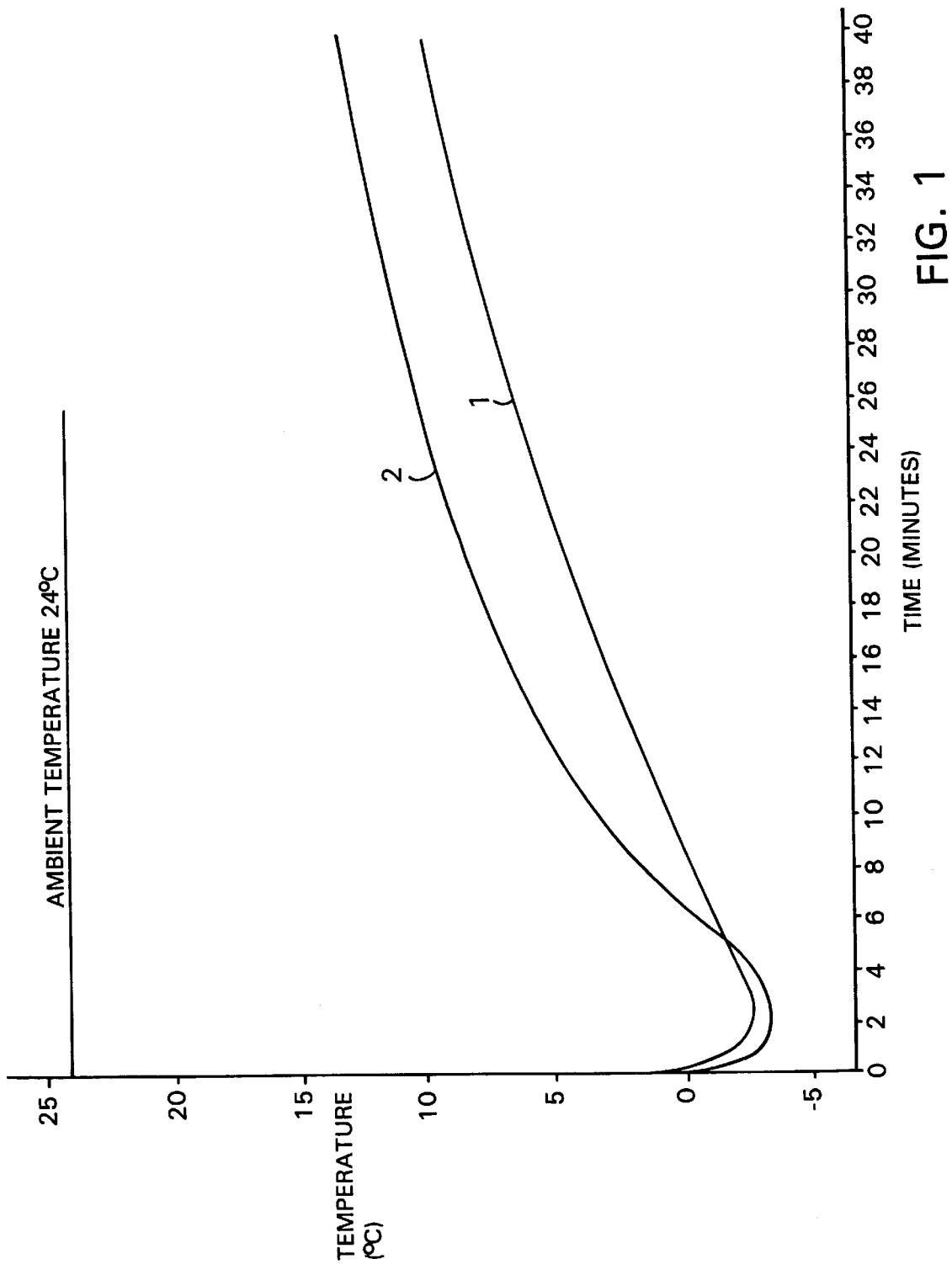
FIG. 1 is a comparison plot of the temperature measured at the pack surface versus time for an embodiment of the gelling cold pack of the invention and a similar non-gelling cold pack.

The present invention is based on the discovery that the gelling agent can be adhered to the cold-generating material used in a cold pack in such a manner that is does not significantly impede or delay the onset of cooling, and that it does not deleteriously affect efficiency. Both the gelling agent and the cold-generating material are provided virtually dust-free, resulting in improved cold pack assembly. Substantial separation of the gelling agent and cold-generating material is avoided during shipping and handling, substantially improving the reliability and reproducibility of cold-pack performance.

Cold-generating Material

The present invention utilizes two materials which, when brought into contact with each other, interact to produce cold. The materials can react either chemically or physically to produce cold.

Chemical reactions which produce cold (endothermic reactions) are those which exhibit a negative heat of reaction. For example, the chemical reaction between an aqueous barium hydroxide solution and ammonium thiocyanate is endothermic, producing cold.

Physical interactions which produce cold are those which exhibit a negative heat of solution. For example, the dissolution in water of inorganic salts such as ammonium nitrate, potassium nitrate, ammonium sulfate, and ammonium chloride produce cold. Further useful cold-generating materials are organic materials such as urea, and other inorganic salts such as ammonium bromide, ammonium iodide, potassium chloride, tin chloride dihydrate, diamminecobalt, dichlorocobalt hexahydrate, and nickel nitrate hexahydrate.

The material with which the cold-generating material interacts is a liquid. The liquid can be aqueous, that is water, or water containing other components, such as hydroxylic and polyhydroxylic species such as alcohols, glycerol, ethylene glycol, propylene glycol and similar compounds.

As will be described below, additional components of the gelling cold packs of the invention can be, for example, phase change materials.

Preferred embodiments of the invention are those in which the cold-generating materials interact physically to produce cold. Preferred cold-generating materials include ammonium nitrate. Ammonium nitrate is widely available in the form of beadlike pellets called prills, either in high- or low-density form. The prills are a composite, particulate material. The low-density form is preferred for gelling cold packs, since it is more readily solubilized, resulting in a desirably fast temperature drop. The low-density prills also contain a clay binder, such as kaolin, at a low percentage by weight (from about 0.5 to about 5% by weight, often from about 1 to 3% by weight). However, the low-density ammonium nitrate prills are more prone to dust production than the high-density prills. This has led gelling cold-pack manufacturers to forego the performance advantages of low-density ammonium nitrate to avoid the complications of manufacture with this material.

Both the high- and low-density ammonium nitrate prills as supplied by a commercial supplier whom we have used (Nitram Inc., Tampa Fla.) were described as having the same specific gravity (i.e., 1.7 g/cc). However, the bulk densities of the two types of prills differ measurably. Low-density ammonium nitrate prills are those which have bulk densities of from about 0.60 to about 0.90 grams per cubic centimeter (g/cc), or from about 0.65 to about 0.85 g/cc. High-density ammonium nitrate prills are those from about 0.90 to about 1.10 g/cc, or from about 0.95 to about 1.05 g/cc. These bulk densities were determined by measuring the volume and weight of samples of high- and low-density ammonium nitrate prills.

In the aqueous-based gelling cold packs of the invention, the cold-generating material is present from about 50 to about 150 grams per 100 mL of water, preferably from about 75 to about 140 grams per 100 mL of water.

Gelling Agent

Gelling agents useful in the present invention are either organic or inorganic; both types are useful in the present invention. Inorganic compounds such as metal oxides, metal alkoxides, or alkali metal salts of metal oxides can be used. These include zinc oxide, tin oxide, titanium oxide, zirconium oxide, and silicates and aluminates in combination with solvents such as water and alcohols.

Preferred gelling agents for use in the invention are organic. Useful organic gelling agents include organic compounds such as carbohydrates including starch; polyacrylamide; polyols such as pentaerythritol; or proteinaceous materials such as dried gelatin. These agents can form gels in combination with solvents such as water, acetone, alcohols, dimethoxytetraglycol. Many further examples of organic- and inorganic-based gel systems are known to those skilled in the art.

Especially preferred are organic gelling agents that form gels upon reaction with aqueous solutions. It has been found that polyhydroxy-containing organic polymer gelling agents work well in the cold packs of the invention. This includes a variety of polysaccharides. Starches have been found to be particularly useful in some of the embodiments of the invention.

Starch comprises a mixture of linear (amylose) and branched (amylopectin) polymers of $\alpha$-D-glucopyranosyl units. Amylose is a linear polymer of D-glucopyranosyl units linked to each other by (1$\rightarrow$4) $\alpha$-glucosidic links. Amylopectin is a highly branched polymer of $\alpha$-D-glucopyranosyl units which are chiefly (1$\rightarrow$4) links, but also containing (1$\rightarrow$6) $\alpha$-glucosidic links located at branch points. Other noncarbohydrate materials isolable from starch include fatty acids, proteins, enzymes, and inorganic materials, which are generally present in small amounts. Starch may be isolated from many sources, including the seeds of corn, waxy corn, wheat, rye, barley, sorghum, or rice, or the roots of such plants as tapioca, potato, or arrowroot, or from the pith of the sago palm tree.

Starches are generally characterized by their gelatinization temperatures, which are the temperatures at which initially thin, opaque starch suspensions become viscous, semiopaque, and finally transparent. Amylose content ranges from almost zero to about 85%, with the majority of the remainder consisting of amylopectin. The thickening of some starch pastes is caused by association of the linear molecules of amylose. Corn starch forms a rigid gel. Waxy starches (with unusually low or no amylose) do not gel in dilute dispersions, but at high concentrations (30%) form reversible gels, which redisperse at 50–60° C.

Starches are also characterized by their degree of substitution. Substituents can be introduced through reactions with free hydroxyl groups. The number of substituent groups introduced is estimated by analysis, and is expressed as percent of functional groups (e.g., nitrogen, phosphorus, chlorine, hydroxyalkyl, or carboxyl), or preferably as degree of substitution. Degree of substitution indicates the number of substituent groups per anhydroglucose unit, and can be calculated from the equation $$DS=(162)(A)/100(B)-(C-1)(A)$$

where DS is the degree of substitution, A is the percent of substituent determined by analysis, B is the formula weight of A, and C is the formula weight of the whole substituent introduced, when different than B. A degree of substitution equal to three means that all free hydroxyl sites on an anhydroglucose unit are substituted.

In the cold packs of the present invention, cold-water gelation is desirable. Pregelatinized starches (including pre-cooked starches) are products which are dried by processes which cause their gelatinization and are useful for such applications. This type of starch swells and disperses in cold water because its granules are disrupted and its molecules not associated to a high degree. This latter effect is a result of rapid dehydration, prior to extensive alignment and association of the molecules. Spray drying, drum drying, puff extrusion and foam heating are suitable methods of producing pregelatinized starch.

Starches, including pregelatinized starches, may be modified by crosslinking, to increase shear resistance, heat resistance, and resistance to extremely high or low hydrogen-ion concentrations. Starches may be partially oxidized to yield improved stability. Starches can be derivatized by inorganic esterification with nitrates, sulfates, phosphates or xanthanates, or by organic esterification through treatment with carboxylic acids, acid anhydrides, acid chlorides, or vinyl esters. Starch ethers can also be formed for use in the present invention.

Another group of cold-water swelling starches are hydrophilic starch derivatives with a high degree of substitution. In such starches, the structure of the granules are either deliberately disrupted in homogeneous reaction systems, or weakened by the substituent groups to the point that the granules hydrate and disperse upon contact with water.

Hydroxyalkylstarches are also suitable as gelling agents in the cold packs of the invention. Such starches include hydroxyethylether hydrogen phosphate starch, and 2-hydroxypropylether hydrogen phosphate starch. At degree of substitution 0.15 to 1.0, such hydroxyalkylstarches are cold-water soluble.

Detailed information on starch gelation is presented in the Encyclopedia of Polymer Science and Technology, v.12, Interscience; John Wiley & Sons, Inc., New York, 1970, pp. 819–847. Methods of starch production and derivitization are well known to those of ordinary skill in the art.

Preferred starches for use in the cold packs of the invention are cold water hydrating starches, which are resistant to temperatures of about −5° C. Suitable starches are available as Binasol 90C, Binasol 81, Soft-Set, Mira-Thik 603, Mira-Thik 606, Mira-Thik 609, Mira-Thik 468, Mira-Thik 469, and Mira-Gel 463 starches (A.E. Staley Mfg. Co., Decatur, Ill.). Especially preferred are Binasol 90C and Mira-Thik 468 starches.

The amount of gelling agent in the gelling cold packs of the present invention can be from about 5 to about 25 grams of gelling agent per 100 mL of water. More than this amount tends to prevent the maximum temperature drop from being achieved, and less than this amount does not provide sufficient gelation in the cold packs. Preferred amounts of gelling agent in the gelling cold packs of the present invention are from about 10 to about 25 grams per 100 mL of water.

Adhering Methods

The gelling agent is adhered to the cold-generating material to produce a low-dust composite. This greatly simplifies pack manufacture, since the gelling agent and the cold-generating material each tends to be quite dusty. This dustiness makes the formation of reliable packaging seals difficult, results in large amounts of wasted ingredients due to the necessity of using dust control systems such as air filters, and greatly increases the risk of explosion in facilities dedicated to the manufacture of gelling cold packs.

The method of adhering the gelling agent to the cold-generating material can be chosen from a number of suitable methods. These include spraying the gelling agent onto the cold-generating material, dipping the cold-generating material into the gelling agent, employing an adhesive material which is applied to the cold-generating material, after which the cold-generating material with adhesive is rolled in, or sprinkled with, gelling agent. The method affixes sufficient gelling agent to the cold-generating material in an adhering manner that substantially inhibits the separation of the particles of gelling agent from the cold-generating material upon handling.

The formation of a continuous coating of gelling agent on the surface of the cold-generating material is undesirable, as this results in an undesirable delay in the onset of reaction between the cold-generating material and the liquid in which it solublizes. Rather, the method of adhering serves to evenly distribute the gelling agent within the cold pack, so that the gelling agent is constrained to be in regions of the pack in which the cold-generating reaction is taking place. Solubilization of the gelling agent is not a limiting step in the generation of cold in the gelling cold packs of the invention.

Prior art gelling cold packs have suffered from the deficiency that the gelling agent becomes localized during shipping or storage, for example, in a corner of the gelling pack, and is subsequently unavailable to perform its function without substantial redistribution by the user. Wetting of the gelling agent is uneven and much of the gelling agent is wasted, as it never fulfills its function of suspending and distributing the cold-generating material. This is wasteful of the gelling agent. The cold packs of the invention have constrained the gelling agent to be dispersed throughout the container upon activation of the gelling cold pack by a user.

Adhering the gelling agent particles to the cold-generating material preferably includes a drying step to inhibit the redistribution of moisture from a hygroscopic cold-generating material to the gelling agent. Such redistribution prior to activation of the pack tends to diminish gelling performance, and therefore the cold-generating performance, of the cold packs of the invention. Drying of the gelling agent-adhered cold-generating material can be carried out by a number of methods including drying in a forced-air oven, drying in an externally-heated rotary drier, or other drying methods known to those skilled in the art.

Optional Ingredients

The gelling cold packs of the invention may optionally contain additional constituents. Among these are phase change materials. Phase change materials store or release latent heat upon a change of phase from a solid phase to a liquid phase, from one solid phase to another solid phase, or vice versa.

Phase change materials act as temperature stabilizers. As the gelling cold pack initially cools, heat is removed from the phase change material, causing it to change phases, preferably to freeze. It will be appreciated that the material is chosen such that it will freeze within the temperature range which can be attained by the device. The frozen phase change material helps to maintain the lowered temperature for a longer time, since the remelting of the phase change material absorbs heat. The heat required to melt the phase change material does not contribute to a rise in temperature of the cold-pack until the phase change material is completely melted. This results in an extension of the effective operating life of the cold packs of the invention.

Suitable phase change materials are those which are liquid at normal ambient temperatures, but which melt approximately at the temperature at which the cold pack is desired to be stabilized. The melting point of a homologous series of paraffinic hydrocarbons is directly related to the number of carbon atoms as shown in the following table:

| Compound Name | Carbon Atoms | Melting Point (° C.) |
| --- | --- | --- |
| n-hexadecane | 16 | 18.2 |
| n-pentadecane | 15 | 10.0 |
| n-tetradecane | 14 | 5.9 |
| n-tridecane | 13 | −5.5 |

Each of the above materials can be separately or combinedly encapsulated, e.g., in microcapsules which range in size from about 1 to about 10 microns and which are formed according to the methods described in any of the references known to those skilled in the art (Vandergaer, J. E., *Microencapsulation: Processes and Applications, Plenum Press*, New York, 1974; Nixon, J. R., *Microencapsulation*, Marcel Dekker, Inc., New York, 1976). Each of the above compounds is most effective when the intended cooling temperature is near its melting point. It will be seen from the foregoing that the performance of a specific gelling cold pack according to the invention can be significantly enhanced by selecting appropriate phase change materials and adding them, in an encapsulated form, to the cold packs of the invention.

Container

The container housing the cold-generating materials, the gelling agent and any optional ingredients is formed to create at least one first zone and at least one second zone. The first zone(s) contain the composite cold-generating material/gelling agent. The second zone(s) contain solvent. These zones must hold the ingredients both before and after operation of the device, and so both zones must be liquid-impermeable. Also, the container must be able to conduct heat from the exterior to the interior, to allow cooling of the exterior of the container, and thereby the cooling of any desired object outside the container.

To allow initiation of the cold-generating interaction, the cold-generating material and the second material with which it interacts must come in contact with each other. This is preferably accomplished in the present invention by opening, selectively perforating, rupturing or otherwise compromising a separator between the zones. In a preferred embodiment, the solvent is a liquid, more preferably aqueous liquid. The aqueous liquid can be transferred into the zone containing the cold-generating material and gelling agent after compromise of the separator. However, it is also contemplated that the cold-generating material and gelling agent can be transferred into the zone containing water after compromise of the separator. Either zone may optionally contain a phase change material.

It is preferred that the separator comprises a material that allows its rupture, perforation, or compromise by manually deformation of the container. In embodiments which comprise more than a single pair of container zones, it is contemplated that the cold pack of the invention comprise an appropriately increased number of separators, so that communication may be established between zones of each type, sufficient to provide the cold desired. A plurality of separators are also possible in embodiments utilizing only a single pair of zones. The invention is not limited by the juxtaposition or configuration of the zones in the cold pack.

Pressure against or along the separator selectively ruptures, perforates, or otherwise compromises the separator, while leaving the outer surfaces of the container, and the surfaces surrounding the container and first and second zones intact. The separator might be comprised of any of a number of functional configurations. In a preferred embodiment, the separator comprises a brittle or weakened wall extending between the first and second zones, which is manually separable, thereby compromising the separator. In another preferred embodiment, the separator is a brittle or weakened wall of a container comprising a first zone which is adapted to be contained within a second zone (a "bag-in-a-bag" configuration).

In another embodiment, the separator is compromised by the use of pull tabs. When pulled, the pull tabs compromise the separator and communication is provided between the first and second zones. In a less preferred embodiment, the separator comprises a hole with a stopper, which is removable when pressure is applied to it. Communication is again provided through the separator. In another embodiment, the separator comprises a wall having a plurality of perforations which rupture under applied pressure and expose the contents of the zones to each other. The separator can likewise consist of a movable disk or cap, pierced or otherwise, or a valve, such as a frangible valve.

Alternatively, the separator is configured to form one or preferably a plurality of fissures or slits when the separator is subjected to external pressure. The fissures can extend inwardly from the edges or perimeter of the separator, or they can be located intermediate the edges or perimeter of the separator. However, any adequate means for compromising the separator is anticipated for use in the present invention. Persons skilled in the art will recognize other possible variants.

The container preferably comprises a thin, flexible, thermally conductive material which is not deleteriously affected by any of the contents of the individual zones, and which is resistant to the temperature to be encountered. Such materials can be polymeric, and include ionomer film (for example, Surlyn® available from DuPont), polyethylene, polypropylene, polyester (such as MYLAR® film obtainable from DuPont) aluminum, aluminized polymer film, and other conventional plastic or other packaging materials suitable for containing cooled liquids, such as rubber, vinyl, or vinyl-coated fabric. Vinyl sealing is typically carried out utilizing a radio frequency sealing process, known to those in the art. A thickness of about 0.02 mm to about 0.1 mm has been found to be satisfactory using clear vinyl. This permits the container to act as a thin-walled envelope that conforms to the shape of its surroundings.

The container preferably comprises an upper layer and a lower layer which are bonded together at the edges to form an hermetically sealed, substantially planar envelope. We most prefer that the separator comprises a wall having weakened or thin areas which rupture when pressure is applied against it.

In a preferred embodiment, the thermally conductive material is a metal foil, such as one composed substantially of aluminum or copper, or a metallized plastic film such as aluminized polyester. The edges of the material are bonded together by any suitable means, for example, soldering, heat sealing, ultrasonic welding, solvent welding, fold sealing, or the use of adhesives. In another preferred embodiment, the material used for the container is an ionomer film.

During fabrication of the cold pack, the container preferably comprises an open end or side at each of the zones for the introduction of the cold-generating material/gelling agent and liquid, respectively. The other sides or edges are sealed before this introduction. After addition of the ingredients to the different zones of the container, the open sides are sealed. The size and shape of the container, as well as the juxtaposition and configuration of zones within the container, will vary according to the application for which it is intended. Alternative assembly procedures are available to properly assemble the cold pack. For example, one type of zone might be vacuum sealed before the loading of the other type of zone, in e.g., an annular arrangement of zones, or the bag-in-a-bag arrangement. A particular embodiment employs a stacked arrangement of zones. The invention is not limited by the arrangement of zones within the container.

After assembly and prior to its use, the cold pack is in a static condition, with the cold pack preferably disposable after a single use. In an alternative embodiment of the present invention, a plurality of first and/or second zones are contemplated for use in the cold pack of the present invention. As previously mentioned, more than one separator could be used in these embodiments, as well as embodiments having only a single pair of zones.

To use the invention, the user compromises or opens the separator. The user then distributes the contents of one zone into the other zone, or vice versa. In preferred embodiments, the contents of the second, liquid-comprising zone are distributed into the first, cold-generating material/gelling agent zone.

There are a number of applications for which the cold packs of the present invention are useful. Travelling in the opposite direction to heat flow, cold may be visualized as being transmitted by convection through the liquid medium in the cold pack to the exterior surfaces of the device, where it is further transmitted to other bodies, according to the specific application for which the heat pack is employed. In such applications, the cold pack is designed to assume the appropriate shapes for these uses. The cold pack is designed to cool food or drink in certain embodiments, for example. The cold pack used to cool food or drink can be designed to meet certain performance criteria such as the attainment of a certain operating temperature within a certain time.

The cold pack of the present invention also finds use in medical facilities, households or recreational locations for therapeutic applications or for relief from overheating. The cold pack may be used to cool strained muscles, joints or ligaments, or to treat or prevent heat exhaustion.

The cold packs of the present invention are easily adapted to be used in surgical or other medical applications, such as in human or veterinary surgery. Because the present cold packs have excellent temperature stability characteristics, patient discomfort and eventual tissue distress due to overcooling are significantly minimized.

Figure 2:
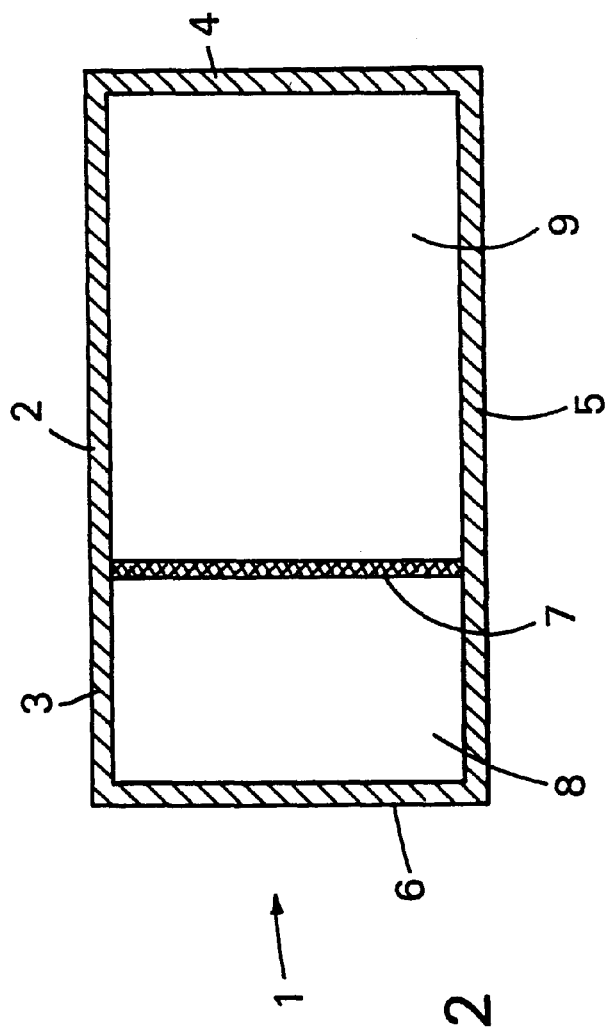
FIG. 2 shows an overhead planar view of the preferred embodiments of a gelling cold pack.
Figure 3:
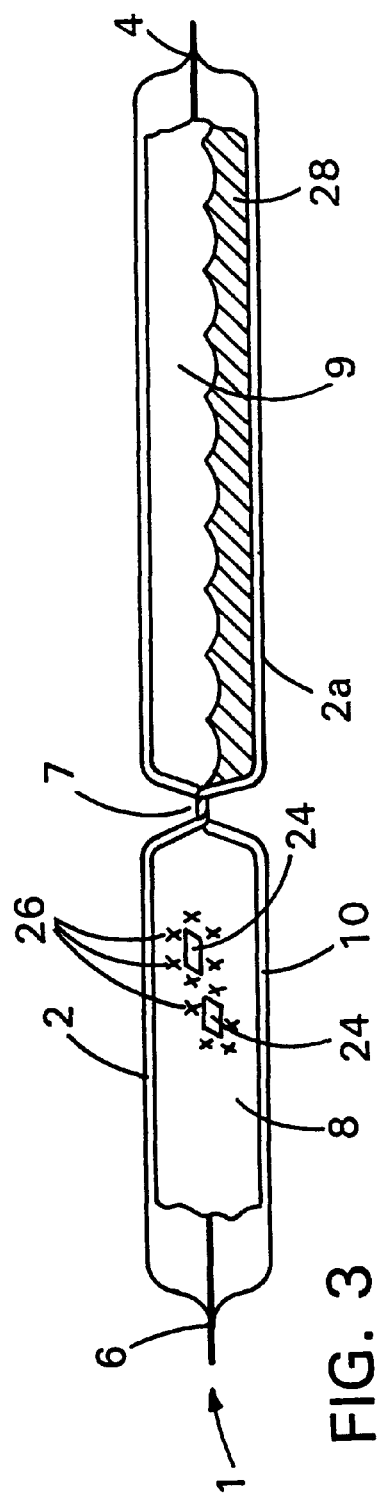
FIG. 3 shows a sectional view of one of the preferred embodiment of a gelling cold pack.

For these and other applications, the cold pack preferably includes a fastening means which allows the initial positioning of the cold pack, e.g., onto a limb. Subsequent activation of the device then takes place without further positional adjustment. Suitable fastening means include straps, adhesive tape, or reusable adherable strips such as VELCRO® strips. The cold pack may be configured as a sleeve which is dimensioned to be placed around a limb, such as the leg of a human, horse, dog, or any other animal. Flat cold packs can be inserted into fabric sleeves or wraps. The sleeve diameter can be adjustable, permitting the use of the same sleeve on a variety of patients. Alternately, the cold pack can be configured as a pad, allowing extensive body surfaces such as the back or chest of a human or animal to be cooled. A particular embodiment is shown in FIG. 2, which illustrates a cold pack in the form of a pad. FIG. 3 is a cut-away side view of this cold pack. Gelling cold pack 1 includes a disposable container having an upper sheet 2 and a lower sheet 2a (visible in FIG. 3). The sheets are sealed together at the edges by edge seals 3, 4, 5, and 6. These edge seals are preferably made so that they are not readily opened by the consumer. A separator 7 is disposed from one edge seal of the cold pack to another edge seal, thus dividing the cold pack into a first zone 8 and a second zone 9. The first zone 8 contains first material 24 for generating cold, and the second zone 9 contains second material 28 which interacts with said first material. Gelling agent 26 is adhered to the first material in the form of a non-continuous coating of gelling agent particles. The cold pack may be activated either before or after contact with the object to be cooled. The term "activation" as used herein refers to compromise or other operation of the separator, mixing the contents of the zones of the disposable container, and thereby initiating interaction of the contents of the zones, as well as manual or other mixing of the contents of the cold pack together to ensure even distribution of the contents and therefore, even cooling.

The cold pack of the present invention is easily adapted to be used in therapeutic applications. Many types of injury are most desirably treated through the application of cold. These include muscle and ligament strains and sprains, as well as such afflictions as rheumatism, arthritis, and the like. Such applications of the cold pack would also require it to be fashioned as a sleeve or a pad, and include fastening means, such as those described above.

The invention also features a method of cooling an object with a self-cooling, disposable gelling cold pack. The method consists of providing a cold pack such as described above, activating the cold pack by compromising the separator, manually or otherwise mixing the contents of the first and second zones together to insure contact of their contents, and putting the cold pack to practical use in cooling an object. This is most effectively accomplished by establishing and maintaining thermal contact between the object and the cold pack. In some embodiments, the cold pack is integral with a container for a substance to be cooled, such as a container for food or drink. In other embodiments, the cold pack is simply added on to the object to be cooled, or adapted to be fit to the object to be cooled.

The invention will be further described in the following examples, which do not limit the scope of the invention described in the claims.

EXAMPLES

The following examples describe some of the properties of some particular embodiments of the claimed invention.

Example 1

Gelling cold pack using low-density ammonium nitrate

In one example, a gelling cold pack of the present invention was made up as follows. One zone of a Surlyn® container contained 110 mL of deionized water. The other zone contained 115 grams of low-density ammonium nitrate prills (Nitram Inc., Tampa Fla.) to which were adhered 21 grams of Binasol 90C starch (A.E. Staley Mfg. Co., Decatur, Ill.) by slightly wetting the ammonium nitrate prills and rolling them in the starch powder. The separator between the zones was made of Surlyn®.

Example 2
Gelling cold pack using high-density ammonium nitrate

In another example, a gelling cold pack of the present invention was made up as in Example 1, with the following modifications. One zone of a Surlyn® container contained 120 mL of deionized water. The other zone contained 115 gras of high-density ammonium nitrate prills, to which were adhered 16 grams of Binasol 90C starch.

Example 3
Comparison of Performance of a Gelling Cold Pack and a Non-Gelling Cold Pack A cold pack according to the ingredients given in Example 1 was compared in performance to a non-gelling cold pack, prepared as follows. 130 grams of low-density ammonium nitrate prills were placed into one zone of a Surlyn® container, with the other zone containing 120 mL of deionized water. Both containers were equipped with frangible seal type separators. The ambient temperature was 24° C. At a time zero, the frangible seals for the gelling cold pack according to Example 1, and the non-gelling cold pack described above were simultaneously compromised. The resulting surface temperatures for the two devices over the next forty minutes are plotted in FIG. 1. Time-temperature plot 1 for the pack according to Example 1 and time-temperature plot 2 for the non-gelling pack are both included in FIG. 1.

As is seen from FIG. 1, the gelling cold-pack of the invention is able to achieve lower temperatures than the non-gelling cold pack for times from 6 minutes after activation to at least 40 minutes after activation. The maximum difference between the lowest temperatures achieved for the two packs is only 3.1° F. (1.7° C.) at 2 minutes after activation. The inventive gelling cold pack clearly shows a cooling effect lifetime which is superior to non-gelling cold packs over this time period. The improved distribution of gelling agent in the inventive gelling cold pack results in substantially improved reliability of gelling and low temperature performance.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A gelling cold pack comprising:
   a disposable container, wherein the container comprises:
      at least one liquid-impermeable, heat-conducting first zone containing a composite particulate first material capable of interacting with a liquid second material to produce cold, to which particles of a gelling agent are adhered as a permeable, non-continuous coating;
      at least one liquid-impermeable, heat-conducting second zone containing said second material with which said first material in said first zone can interact to produce cold;
      a separator disposed between said first and second zones, the separator being manually operable to provide communication between said zones,
      wherein communication between the zones initiates gelation of the gelling agent to produce a gel in the container, and wherein said communication initiates the interaction of said first and said second materials, resulting in the generation of cold within the container.

2. The gelling cold pack of claim 1, wherein the second material is an aqueous solution.

3. The gelling cold pack of claim 1, wherein the first material is selected from the group consisting of ammonium nitrate, urea, ammonium bromide, ammonium iodide, potassium chloride, tin chloride dihydrate, diamminecobalt, dichlorocobalt hexahydrate, and nickel nitrate hexahydrate.

4. The gelling cold pack of claim 3, wherein the first material is ammonium nitrate.

5. The gelling cold pack of claim 4, wherein the ammonium nitrate is in the form of at least one low-density prill.

6. The gelling cold pack of claim 4, wherein the ammonium nitrate prill has a bulk density of less than 0.90 grams per cubic centimeter.

7. The gelling cold pack of claim 1, wherein the gelling agent is a starch.

8. The gelling cold pack of claim 7, wherein the gelling agent is sprayed onto the first material.

9. The gelling cold pack of claim 7, further comprising an adhesive to adhere the gelling agent to the first material.

10. The gelling cold pack of claim 1, wherein the container comprises a thin-walled envelope that conforms to the shape of its surroundings.

11. The gelling cold pack of claim 9, wherein the container comprises a polymeric material.

12. The gelling cold pack of claim 1, wherein the separator is a single-use frangible membrane.

13. The gelling cold pack of claim 1, further comprising encapsulated phase change material.

14. A method of cooling objects, comprising the steps:
   a) providing the gelling cold pack of claim 1 in contact with an object to be cooled;
   b) compromising the separator to provide communication between the zones, thereby initiating interaction between the first and second materials, resulting in the generation of cold within the container.

15. The method of claim 14, wherein the object to be cooled is a part of the body of an animal or human.

16. The method of claim 14, wherein the object to be cooled is an item of food or drink.

17. A gelling cold pack comprising:
   a disposable polymeric container, wherein the container comprises:
      at least one liquid-impermeable, heat-conducting first zone containing starch adhered to low-density ammonium nitrate;
      at least one liquid-impermeable, heat-conducting second zone containing water;
      a single-use frangible membrane disposed between said first and second zones, the separator being operable to provide communication between said zones,
      wherein communication between the zones initiates gelation of the starch within the container to produce a starch gel in the container, and initiates the interaction of the ammonium nitrate and water, resulting in the generation of cold within the container.

* * * * *